United States Patent [19]

Stouffer

[11] Patent Number: 5,303,708
[45] Date of Patent: Apr. 19, 1994

[54] GRADING OF POULTRY CARCASSES WITH ULTRASOUND

[75] Inventor: James R. Stouffer, Ithaca, N.Y.

[73] Assignee: Animal Ultrasound Services, Inc., Ithaca, N.Y.

[21] Appl. No.: 919,822

[22] Filed: Jul. 27, 1992

[51] Int. Cl.$^5$ .................................................. A61B 8/00
[52] U.S. Cl. ............................ 128/660.01; 128/660.07
[58] Field of Search ....................... 128/660.01, 660.07; 73/602

[56] References Cited

U.S. PATENT DOCUMENTS

| | | | |
|---|---|---|---|
| 3,496,764 | 2/1970 | Stouffer | 128/660.09 |
| 3,603,303 | 9/1971 | Stouffer | 128/660.01 |
| 3,688,564 | 9/1972 | McDicken | 73/620 |
| 3,709,029 | 1/1973 | Hurwitz | 73/624 |
| 3,722,263 | 3/1973 | Hautaniemi et al. | 73/622 |
| 3,742,756 | 7/1973 | Seager | 73/640 |
| 3,854,471 | 12/1974 | Wild | 128/660.09 |
| 3,964,296 | 6/1976 | Matzuk | 73/607 |
| 3,964,297 | 6/1976 | Jorgensen et al. | 73/609 |
| 4,094,306 | 6/1978 | Kossoff | 73/607 |
| 4,099,420 | 7/1978 | Stouffer et al. | 73/629 |
| 4,130,112 | 12/1978 | Frazer | 128/661.02 |

(List continued on next page.)

FOREIGN PATENT DOCUMENTS 0337661 10/1989 European Pat. Off. .

OTHER PUBLICATIONS

Ultrasonics For Live Lamb And Carcass Evaluation, J. R. Stouffer 1988 Proceeding Sheep Industry Development Program, Denver, Col.

Syllabus-Animal Ultrasound Seminar & Wet-Lab-Oct. 13-15, 1989.

Untrasonographic Evaluation Of The Urinary System And Prostrate Gland In The Dog And Cat-R. Badertscher-Veterinary Imaging Professional.

Meat And Poultry Inspection-National Academy Press-1985.

Tendon And Ligament Ultrasound In The Equine Athlete-A. Kent Allen-Allen-Schneigder Equine Hospital.

A Review Of Potential New Methods Of On-Line Port Carcass Evaluation-Forrest et al-J. Anim. Sci 1989-67:2164-2170.

A Review Of Ultrasonic Applications In Animal Science-J. R. Stouffer-Journal of Clinical Ultrasound-vol. 5, Apr. 1977.

Ultrasound For Animal Evaluation-J. R. Stouffer-New York's Food and Life Sciences-vol. 10 No. 3, 1977.

Objective Technical Methods For Determining Carcass Value In Live Animals With Special Emphasis On Ultrasonics-J. R. Stouffer-World Review of Animal Production-1966.

Mild Exercise-Effect On Body Composition And Metabolism Stouffer et al-N. Y. State Journal of Med.-Aug. 1974.

Relationship Of Ultrasonic Measurements And W-X-Rays To Body Composition-J. R. Stouffer-Animals of

(List continued on next page.)

Primary Examiner—Francis Jaworski
Attorney, Agent, or Firm—Michael F. Brown; Christopher A. Michaels; Ralph R. Barnard

[57] ABSTRACT

The present invention includes method and apparatus for grading a poultry carcass intended for human consumption. An ultrasound machine is provided which includes a probe for transmitting and receiving ultrasound signals such that the machine is capable of producing a image of a breast muscle of the carcass. The probe is positioned on the carcass parallel to the keel such that the image of the breast muscle of the carcass is detected by the ultrasound machine. A breast muscle size indicator of the breast muscle is determined from the detected image. The calculation of a grade for the carcass is based upon the ratio of the indicator to the weight of the carcass. The determination of the breast muscle size indicator can be performed by an image analyzer and pattern recognition equipment modified to recognize the breast muscle image. The probe can be positioned automatically by probe location equipment automatically.

9 Claims, 6 Drawing Sheets

U.S. PATENT DOCUMENTS

| | | | |
|---|---|---|---|
| 4,186,747 | 2/1980 | Iinuma | 128/660.08 |
| 4,359,055 | 11/1982 | Carlson | 128/661.03 |
| 4,359,056 | 11/1982 | Carlson | 128/661.03 |
| 4,545,385 | 10/1985 | Pirschel | 128/660.09 |
| 4,603,701 | 8/1986 | Chen | 128/662.03 |
| 4,664,124 | 5/1987 | Ingle et al. | 128/660.02 |
| 4,772,346 | 2/1988 | Chen | 156/89 |
| 4,785,817 | 11/1988 | Stouffer | 128/660.07 |
| 4,870,970 | 10/1989 | Gray et al. | 128/660.09 |
| 4,931,933 | 6/1990 | Chen et al. | 364/409 |
| 5,014,713 | 5/1991 | Roper et al. | 128/664 |
| 5,028,440 | 7/1991 | Nissen | 426/2 |
| 5,078,147 | 1/1992 | Reid | 128/661.01 |
| 5,079,951 | 1/1992 | Raymond et al. | 73/602 |
| 5,140,988 | 8/1992 | Stouffer et al. | 128/660.01 |

OTHER PUBLICATIONS the N.Y. Academy of Sci, vol. 110, Part I. pp. 31-3-9-Sep. 1963.

Ultrasonics For Evaluation Of Live Animal And Carcass Composition–J. R. Stouffer–Twelfth Research Conference–pp. 81-87.

Development And Application Of Ultrasonic Methods For Measuring Fat Thickness And Rib-Eye Area In Cattle And Hogs–J. R. Stouffer et al–Journal of Animal Sci., vol. 20, No. 4, Nov. 1961.

Ultrasonic News–Winter 1960–vol. IV No. 4.

Comparison Of Methods Used For Carcass Evaluation In Swine Doornenbal et al–Jou. of Ani. Sci., vol. 21, No. 3, Aug., 1962.

Techniques For The Estimation Of the Composition Of Meat Animals–J. R. Stouffer, pp. 207-219.

Status Of The Application Of Ultrasonics In Meat Animal Evaluation–J. R. Stouffer–pp. 161-173.

Ultrasonic Research In Europe–J. R. Stouffer–Mar.-Aug. 1962.

The Ultrasonic Approach To Measuring Fat And Muscling In Live Beef Cattle–J. R. Stouffer–pp. 34-35.

Carcass Evaluation And Its Research Applications–J. R. Stouffer–1961–pp. 32-36.

Application Of Ultrasound In The Livestock And Meat Industry J. R. Stouffer–pp. 310-315.

Meat Evaluation In Live Animals–J. R. Stouffer–Frontiers in Food Research, Cornell University, Apr. 12-13, 1966, pp. 102-108.

Muscle Metabolism And Real-Time Ultrasound Measurement Of Muscle And Subcutaneous Adipose Tissue Growth In Lambs Fed Diets Containing A Beta-Agonist–Stouffer et al–J. Anim. Sci. 1986, 63:1410-1417.

Estimating Fatness In Horses And Ponies–Stouffer et al. Jour. Anim. Sci., vol. 43, No. 4 (1976).

Syllabus–2nd Annual Aium Animal Ultrasound Seminar & Wet-Lab American Institute of ultrasound in Medicine–1990.

The Use Of Ultrasound To Predict The Carcass Composition Of Live Cattle–A Review–Animals Breeding Abstracts–G. Simm, vol. 51, No. 12, 1983.

Ultrasonic Determination Of Body Composition–J. R. Stouffer Dec. 1968.

Studies On The Pathogenesis Of Staphylococcal Osteomyelitis In Chickens, –I. Effect of Stress on Experimentally Induced Osteomyelitis Mutalib et al–Avian Dis., vol. 27, No. 1, Jan.–Mar. 1983 pp. 141-156.

Ultrasonics of Postmortem Detection of Animal Diseases And Abnormalities–J. R. Stouffer–Seminar for FSIS–USDA–Sep. 18, 1985.

Die Anwendung Non Ultraschallmessungen In Den USA–J. R. Stouffer, pp. 64-70.

Real Time Ultrasound Evaluation–J. R. Stouffer–Jun. 1988.

Relationships Of Empty-Body Composition And Fat Distribution To Live Animal And Carcass Measurements In Bos Indicus–Bos Taurus Crossred Cows–Holloway et al–pp. 1818-1826.

"An Evaluation Of Indices Of Carcass Yield, Physical Composition And Chemical Composition In Swine; And Ultrasonic Measurement Of The Longissimus Dorsi Area And Fat Thickness In Beef And Swine", Wayne Gillis, Jan., 1971.

"Pregnancy Detection And Changes During Gestation In Swine Determined With Ultrasound", T. Wongkhalaung, Jun. 1975.

"Grading Hog Carcasses: The CSB Ultra-Meater", CSB System.

"Commercial Adaption Of Ultrasonography To Predict Pork Carcass Compositions From Live Animal And Carcass Measurements" Gresham et al, J. Anim. Sci, 1992, pp. 631-639.

"Using Ultrasound Objectively Evaluate Composition And Quality Of Livestock", James Stouffer, 21st Century Concepts, pp. 49-53.

"Scamogram", Model 722, Ithaco, Inc., Ultrasonic Animal Scanner.

"Ultrasound For Disease Detection In Animals", J. Stouffer Seminar for FSIS–USDA, Sep. 18, 1985.

GRADING OF POULTRY CARCASSES WITH ULTRASOUND

FIELD OF THE INVENTION

The present invention relates to methods and apparatus for grading poultry carcasses for human consumption, and more particularly relates to methods and apparatus for grading poultry carcasses using ultrasound.

BACKGROUND OF THE INVENTION

Many different types of evaluations are carried out on meat products before they are approved for commercial sale. Some of these procedures involve a system of grading depending upon fat and muscle content and distribution, while others involve condemnation decisions.

Various types of ultrasonic apparatus for examining the internal structure of humans and animals are, of course, well known in the prior art. The use of ultrasonic techniques for inspecting live animals for fat thickness has long been proposed, particularly in percentage of fat or lean, so that the fat indication provides a reasonable indication of carcass composition.

The advantage of using ultrasonic apparatus to inspect and grade livestock are numerous. Primarily, an animal's value can be accurately assessed without causing any damage to the carcass. In meat animals a grading determination is based upon the relative quantity of fat or muscle within a normal set of parameters. The normal set of parameters are the same for each animal within a particular species (e.g. the number of fat or muscle layers) whereas the proportion each type of tissue within these parameters differs for each individual animal. Ultrasound techniques have been used extensively to determine grading characteristics of livestock.

Currently poultry carcasses are graded A, B, or C subjectively based primarily upon general appearance, fleshiness and freedom from defects, torn skin and other blemishes. However there has been no practical way of accurately predicting the relative ratio of muscle to bone and the overall muscle composition of poultry carcass without dissection. As the breast is usually considerably the most valuable portion of poultry, it would be extremely valuable to provide a meaningful grading system based upon the size of the breast muscle to the overall weight of the carcass.

The industry is in need of a method of grading for poultry that provides a meaningful, accurate information on the size of the breast muscle to the weight of the carcass.

SUMMARY OF THE INVENTION

It is a primary objective of this invention to provide a new and improved apparatus and method for grading poultry carcasses intended for human consumption.

It is a further objective of this invention to provide a new and improved apparatus and method for grading poultry carcasses intended for human consumption using ultrasound.

It is a further objective of this invention to provide a new and improved apparatus and method for rapidly and accurately measuring the thickness or amount of breast muscle for use in grading poultry carcasses intended for human consumption using ultrasound.

One discovery of the present invention is that ultrasound technology can be used to grade poultry carcasses. By correct placement of an ultrasonic linear transducer (probe) and interpretation of the breast muscle image of the carcass an objective grade can be assigned.

The present invention includes method and apparatus for grading a poultry carcass intended for human consumption. An ultrasound machine is provided which includes a probe for transmitting and receiving ultrasound signals such that the machine is capable of producing a image of a breast muscle of the carcass. The probe is positioned on the carcass parallel or perpendicular to the keel such that the image of the breast muscle of the carcass is detected by the ultrasound machine. A breast muscle size indicator of the breast muscle is determined from the detected image. The calculation of a grade for the carcass is based upon the ratio of the indicator to the weight of the carcass. The determination of the breast muscle size indicator can be performed by an image analyzer and pattern recognition equipment modified to recognize the breast muscle image. The probe can be positioned automatically to probe location equipment automatically.

These and other objects, features and advantages of the present invention should become apparent from the following description when taken in conjunction with the accompanying drawings.

DETAILED DESCRIPTION OF THE PREFERRED EMBODIMENT

For the purposes of promoting an understanding of the teachings of the present invention, references will now be made to the embodiments illustrated in the drawings and specific language will be used to describe these embodiments. It will nevertheless be understood that no limitation of the scope of the invention is thereby intended, alterations and further applications of the teachings of the present invention as illustrated and described hereinabove is anticipated by those skilled in this art.

As used herein, the term "poultry" means all turkeys, chickens, duck, and other fowl normally included within the term poultry. As used herein, the term "probe" or "transducer" refer to a linear array transducer for ultrasonic equipment with a scan line that is parallel to the direction of the transducer. As used herein, the term "breast muscle size indicator" means a measurement of the depth or area of the breast muscle as shown in an ultrasonic image with the understanding that the indicator is not a measurement of the whole muscle but only of the portion of the image corresponding to breast muscle.

Referring now to FIGS. 1-6, the method and apparatus are shown in various embodiments. After a poultry animal has been bled and defeathered in the slaughter process, its grade or value can be ascertained by determining the percent yield of breast as a measure of its total meatiness. FIGS. 1a and 1b are perspective views of an individual using an ultrasound grading station 1 as taught by the present invention. The individual is positioning an ultrasonic probe 2 on a poultry carcass 3. The inspection station 1 includes an ultrasonic scanner and monitor 4, attached to the probe 2 for transmitting and receiving ultrasonic signals, the probe is positioned on the carcass 3 such that an image of the breast muscle of the carcass 3 being examined is shown on the display 5. This can be connected to a recorder apparatus 6 for recording these images for later analysis or use in creating a reference pool.

Figure 1A:
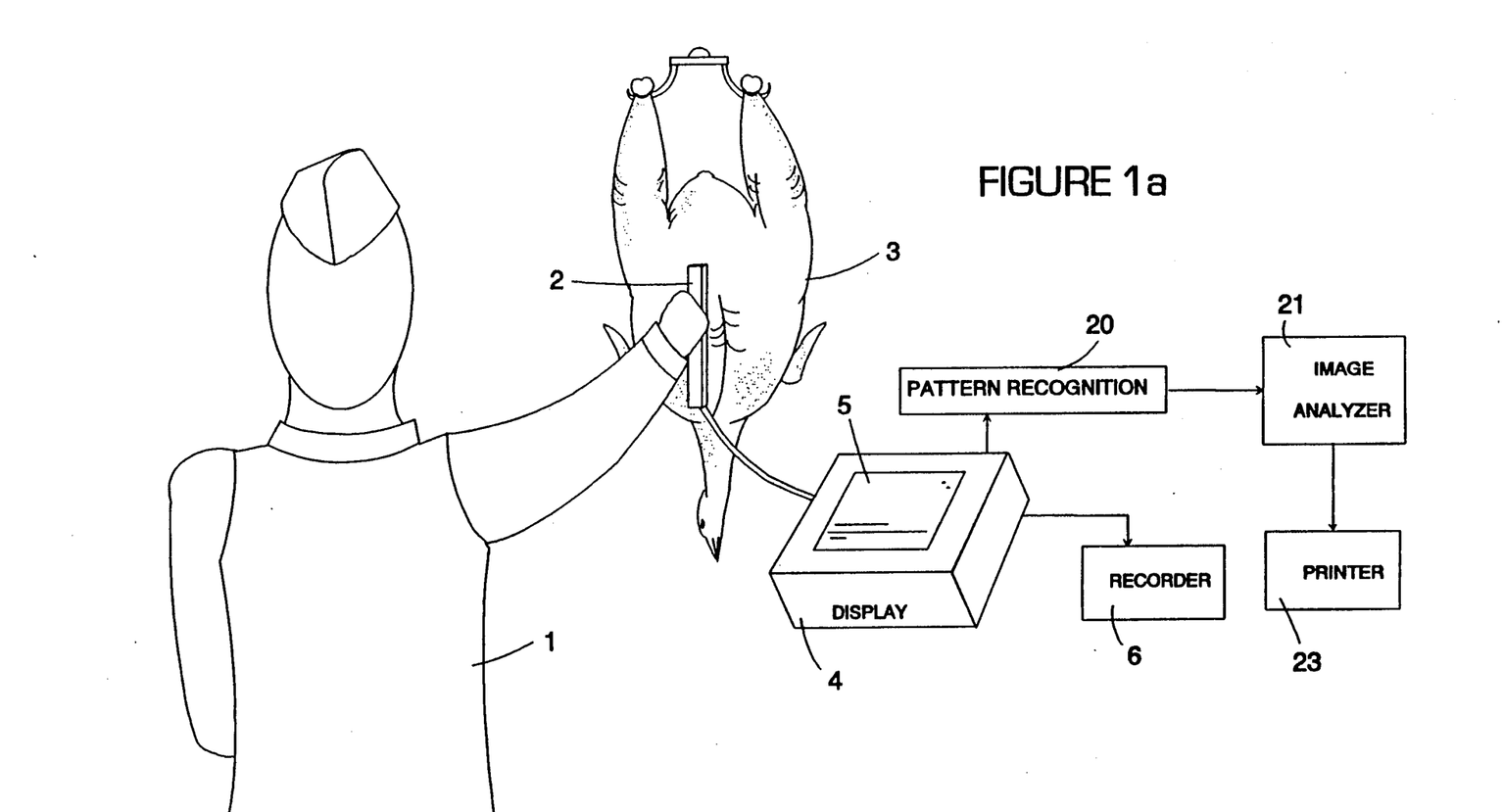
FIGS. 1a and 1b are perspective views of an individual positioning an ultrasonic probe on a poultry carcass.
Figure 1B:
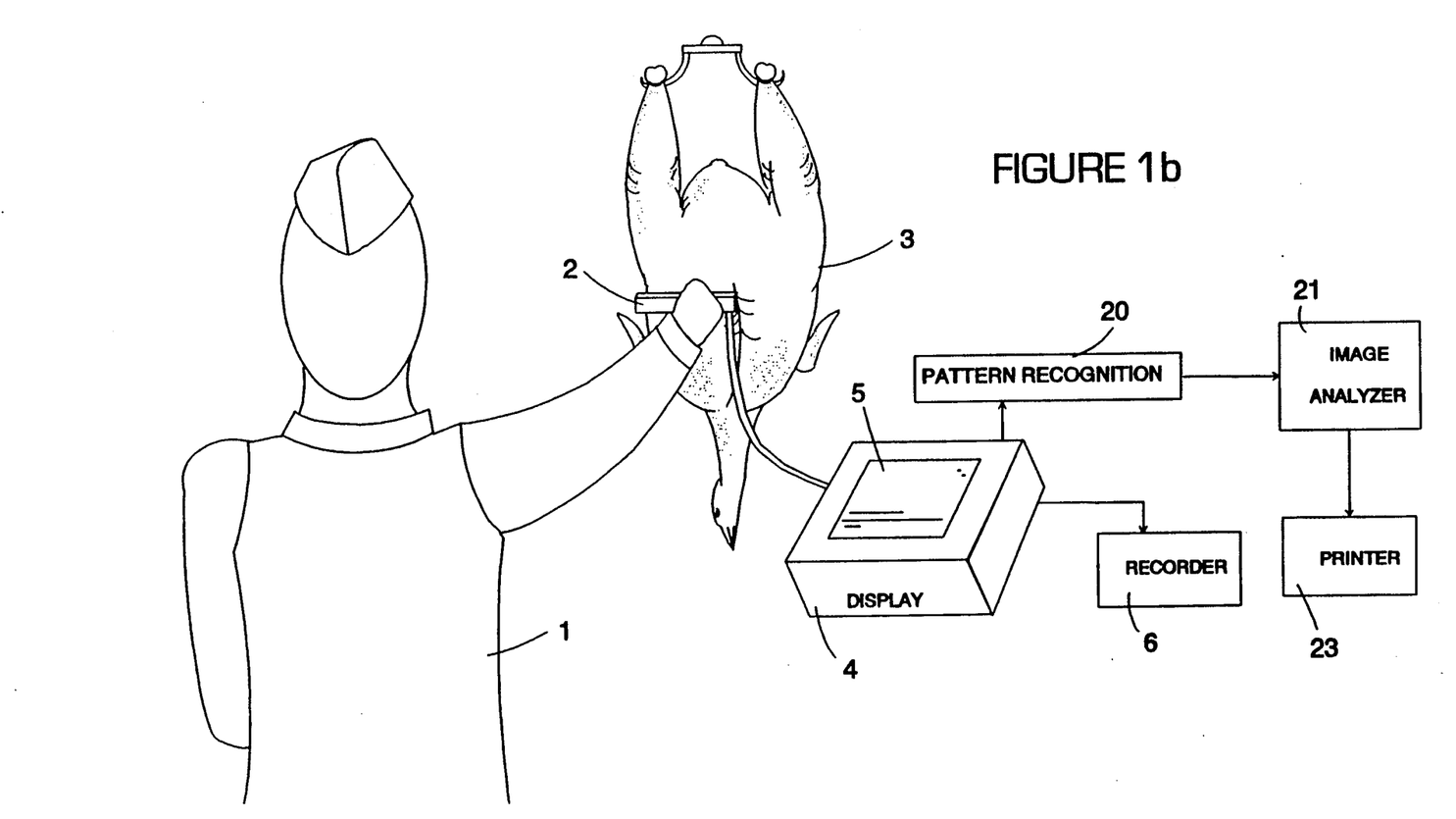

After the individual positions the ultrasonic transducer probe 2 on the carcass 3 such that the breast muscle image is shown on the display, the image on the display 5 is analyzed to determine the depth or area of portion of the image corresponding to breast muscle. The measurements provided through ultrasonic image analysis are several depth readings at predetermined positions relative to the leading edge of the keel bone. The measurements are indicators are the plumpness, fullness and shape of the muscle which are used to predict breast weight. By dividing breast weight (or the indicator directly) by total carcass weight gives percentage of breast yield for an objective grade and value.

Making contact with the tissues of the breast muscle with an ultrasonic transducer probe 2 provides a real time (15× second) image that shows the breast muscle. The cross section of the breast muscle is detected using ultrasound, which does not require the carcasses to be cut open, thereby providing industry with accurate information concerning product value and savings in labor. As shown in FIG. 1a, a linear transducer array probe 2 is placed over the breast parallel to the keel 10, perpendicular to the skin surface and about 5 centimeters to the side (being sure that the tissue to probe surfaces are moist, i.e. adequate couplant). As shown in FIG. 1b, a linear transducer array probe 2 is placed over the breast perpendicular to the keel 10, perpendicular to the skin surface and starting at the keel 10 across the breast muscle. The direction and orientation of the probe 2 are critical for a good image.

Figure 2A:
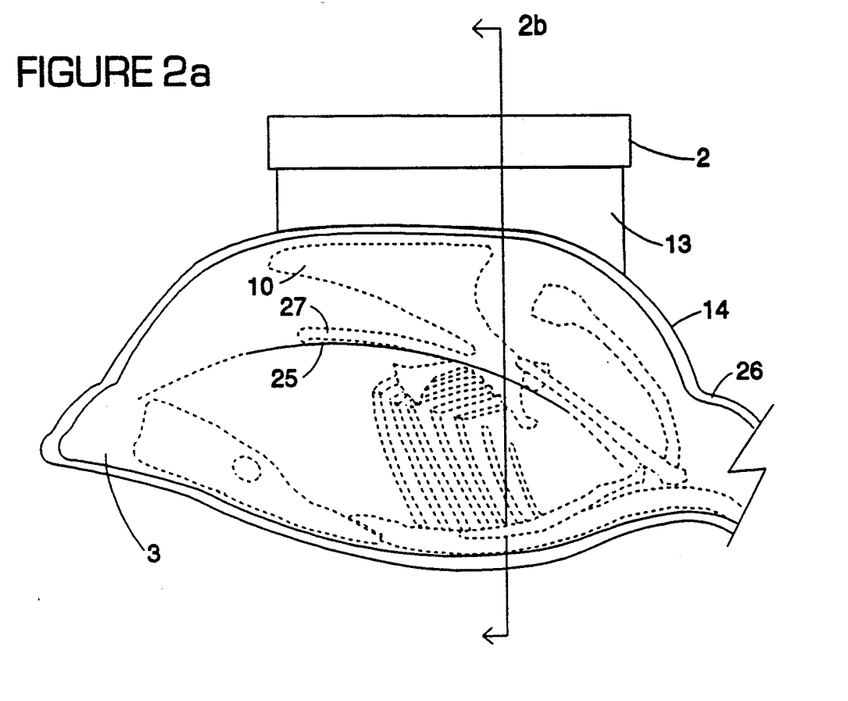
FIGS. 2a and 2b are cross-sectional views of a poultry carcass showing proper positioning of an ultrasonic probe.
Figure 2B:
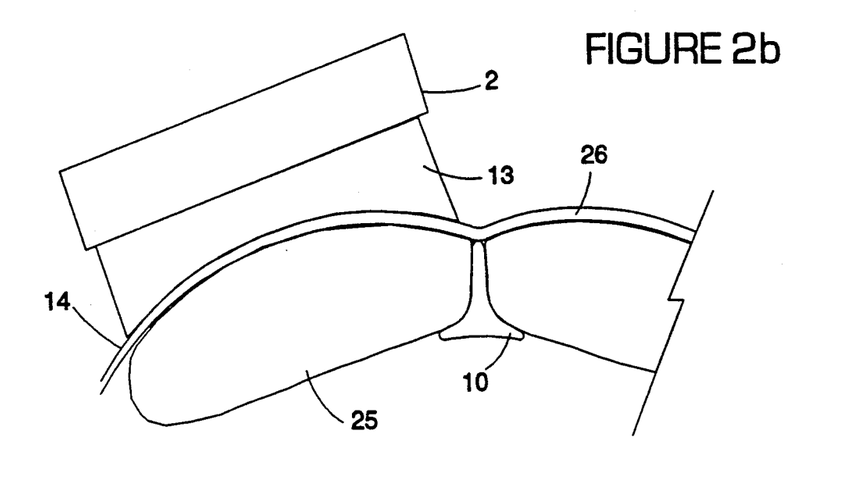

FIGS. 2a and 2b are cross-sectional views of a breast muscle 11 showing proper positioning of an ultrasonic probe 2. The probe 2 includes a standoff gel 13 which is flexible to allow unbroken contact with the skin 14. This standoff gel is generally made of a polyvinyl chloride gel with a resin additive. Superflab ™ and Flexgel ™ are both types of gels used for this purpose. The gel 13 is slightly curved for good contact with the curved tissue and skin 14. In an assembly line application, gels 13 could be shaped to insure uniform and accurate positioning. Adequate couplant fluid must also be used to insure that there is no air between the standoff gel 13 and the skin 14. Water is an adequate couplant fluid for examining poultry with ultrasound. The carcasses 3 could be already wet from other processing or could be automatically moistened before examination. FIG. 2a show the proper positioning of the probe 2 on the breast muscle parallel and slightly away from the keel 10. FIG. 2b shows the proper positioning of the probe 2 on the breast muscle perpendicular to the keel 10.

Experienced ultrasound technologists will be able to position a probe 2 to achieve the desired image cross-section quite easily. The individual can use a 17.2 cm linear array transducer probe 2 and most of the breast muscle should be visible. Any ultrasound capable of producing at least a cross-sectional image could be used. One specific ultrasound machine that could be used to practice the teachings of the present invention is the Aloka 500V with transducer probe UST 5044-3.5 or 5011-3.5. The specific frequency (i.e. 3.5 or 5.0, etc.) and length of the transducer used is also a matter of choice, depending on the depth of the image desired, the amount of clarity needed and the length of the image desired for examination. The grading method taught herein, can be easily detected with deep probing frequencies which are generally less clear, yet the breast muscle to be examined is relatively new the surface such that less deeply probing frequencies can be used if greater clarity is desired.

The individual interprets the image or a pattern recognition system 20 could be operatively connected to the display 5. The pattern recognition system 20 could also be connected to an image analyzer 21. The pattern recognition equipment 20 identifies a pattern of muscle composition of said carcass shown on said image. This can be accomplished by using a standard stand off gel 13 and detecting the bottom edge 25 of the breast muscle 26. A variety of edge detection algorithms exist and are being developed for use in automatic ultrasound detection equipment. Such an algorithm could use a series of five depth measurements at predetermined positions relative to the leading edge of the keel bone 10. The image analyzer 21 would take these measurements and determine a breast muscle size indicator from the pattern of muscle composition and calculate a grade for the carcass based upon the ratio of the indicator to the weight of the carcass. Alternatively, the indicator could provided an estimation of breast weight, but the end grade determination would still be based upon the indicator. One system that could be programmed to handle the image analysis is an AniMorph image analyzer. The pattern recognition equipment 20 and the image analyzer 21 could physically be incorporated into a single piece of equipment, however, each function must be performed. The pattern recognition equipment 20 selects appropriate portions of the image for analysis recognizes edges and the image analyzer 21 analyzes the measurements and provides an output of the grade assigned to the carcass.

The pattern recognition software for detecting edges could be relatively simple because the bone 27 below the breast muscle 26 casts a shadow over the rest of the image, so that last interface on the display is going to be the bone 27 and the bottom of the breast muscle 25. Once the lowest interface is determined, the approximate line of the breast muscle 25 is known. An indicator is being provided which may or may not be the actual dimensions of the breast muscle, however in all circumstances the indicator will be highly correlated with actual breast muscle size such that the indicator will useful for a grading determination. The levels of grading and the values assessed to each grade would be empirically determined by the poultry industry. The printer 23 could be used to provide reports of grading, the number of carcasses examined, hourly rate of examination, etc.

Figure 3:
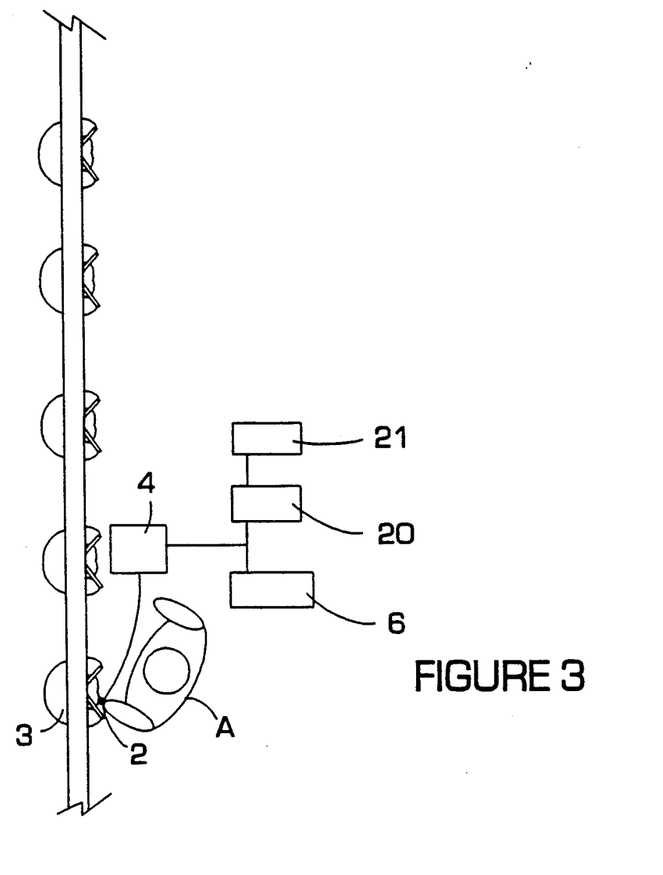
FIG. 3 is a perspective view of individuals implementing the apparatus and methods taught by the present invention to grade poultry carcasses on an assembly line.

FIG. 3 shows one possible implementation of the apparatus and methods taught by the present invention in the grading of poultry carcasses on an assembly line. The poultry carcasses 3 are on a main assembly line 30 and an individual A quickly inspects each one using ultrasound equipment 4.

Figure 4A:
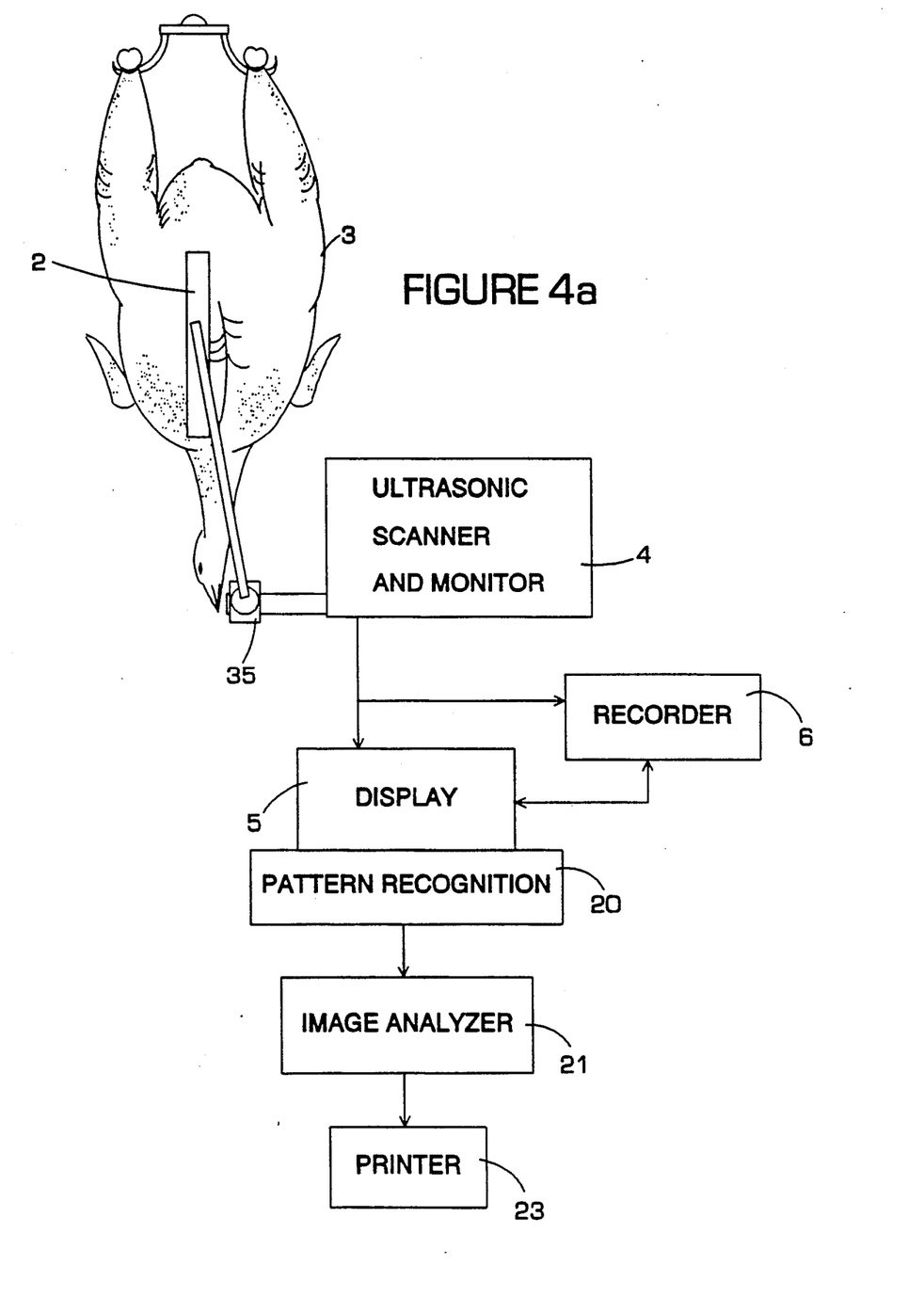
FIGS. 4a and 4b are perspective views of one possible embodiment of an automated ultrasound grading station positioning an ultrasonic probe on a poultry carcass.
Figure 4B:
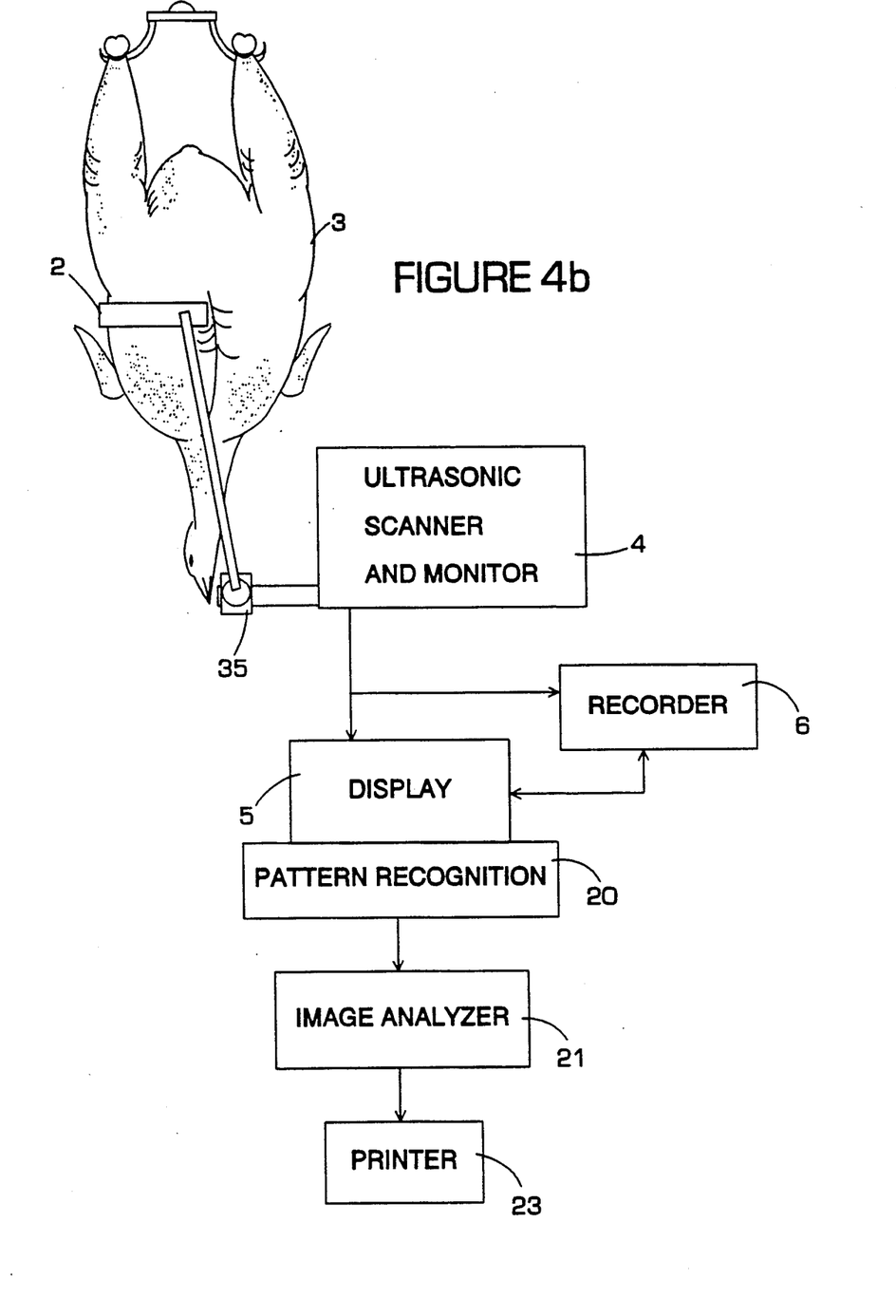

FIGS. 4a and 4b show an automated inspection station in greater detail. As shown, the probe 2 is mounted on a spring loaded base 35 such that the probe 2 engages the skin 14 over the breast muscle. This system could be used to examine every carcass 3. The probe 2 creates images fast enough such that the carcasses 3 could move along at a faster rate than would be possible by manual examination, thereby decreasing processing time. As shown in FIG. 4a, a linear transducer array probe 2 is placed over the breast parallel to the keel 10, perpendicular to the skin surface and about 5 centimeters to the side. As shown in FIG. 4b, a linear transducer array probe 2 is placed over the breast perpendicular to the keel 10, perpendicular to the skin surface and starting at the keel 10 across the breast muscle.

The method of grading includes providing an ultrasound machine which includes a probe for transmitting and receiving ultrasound signals such that the machine is capable of producing a image of a breast muscle of the carcass. The probe is positioned on the carcass parallel or perpendicular to the keel such that the image of the breast muscle of the carcass is detected by the ultrasound machine. A breast muscle size indicator of the breast muscle is determined from the detected image. The calculation of a grade for the carcass is based upon the ratio of the indicator to the weight of the carcass. The determination of the breast muscle size indicator can be performed by an image analyzer and pattern recognition equipment modified to recognize the breast muscle image. The probe can be positioned automatically by probe location equipment automatically.

The foregoing description has been directed to particular embodiments of the invention in accordance with the requirements of the Patent Statutes for the purposes of illustration and explanation. It will be apparent, however, to those skilled in this art that many modifications and changes will be possible without departure from the scope and spirit of the invention. It is intended that the following claims be interpreted to embrace all such modifications.

I claim:

1. A method of grading a poultry carcass intended for human consumption, comprising:
   a) providing an ultrasound machine, including a probe for transmitting and receiving ultrasound signals such that said machine is capable of producing a image of a breast muscle of said carcass;
   b) positioning said probe on said carcass such that said image of said breast muscle of said carcass is detected by said ultrasound machine;
   c) determining a breast muscle size indicator of said breast muscle from said detected image; and
   d) calculating a grade for said carcass based upon a ratio of said indicator to a weight of said carcass.

2. The method of claim 1 wherein said determination of said breast muscle size indicator is performed by an image analyzer and pattern recognition equipment modified to recognize said breast muscle image.

3. The method of claim 1 wherein the probe is positioned parallel to a keel of said carcass.

4. The method of claim 1 wherein the probe is positioned perpendicular to a keel of said carcass.

5. The method of claim 1 wherein said probe is positioned automatically by probe location equipment.

6. An apparatus for grading a poultry carcass intended for human consumption, comprising:
   a) an ultrasound machine, including a probe for transmitting and receiving ultrasound signals, wherein said probe can be positioned on said carcass such that an image of a breast muscle of said carcass is detected by said ultrasound machine;
   b) pattern recognition equipment for determining and identifying a pattern of muscle composition of said carcass shown on said image;
   c) an image analyzer for determining a breast muscle size indicator from said pattern of muscle composition and for calculating a grade for said carcass based upon a ratio of said indicator to a weight of said carcass; and
   d) means for indicating said grade for said carcass.

7. The apparatus of claim 6 wherein said probe is positioned parallel to a keel of said carcass.

8. The apparatus of claim 6 wherein said probe is positioned perpendicular to a keel of said carcass.

9. The apparatus of claim 6 further comprising probe location equipment for automatically positioning said probe on said carcass.

* * * * *